United States Patent
Satyanarayana et al.

(10) Patent No.: US 11,452,722 B2
(45) Date of Patent: Sep. 27, 2022

(54) STABLE PHARMACEUTICAL COMPOSITIONS COMPRISING LENALIDOMIDE

(71) Applicant: NATCO PHARMA LIMITED, Hyderabad (IN)

(72) Inventors: Vattikuti Satyanarayana, Hyderabad (IN); Bhavanasi Krishna Murthy, Hyderabad (IN); Vemuri Venkata Suresh Babu, Hyderabad (IN); Bhat Pavan, Hyderabad (IN); Nannapaneni Venkaiah Chowdary, Hyderabad (IN)

(73) Assignee: NATCO PHARMA LIMITED, Hyderabad (IN)

( * ) Notice: Subject to any disclaimer, the term of this patent is extended or adjusted under 35 U.S.C. 154(b) by 0 days.

(21) Appl. No.: 16/962,131

(22) PCT Filed: Jan. 7, 2019

(86) PCT No.: PCT/IN2019/050012
§ 371 (c)(1),
(2) Date: Jul. 14, 2020

(87) PCT Pub. No.: WO2019/138424
PCT Pub. Date: Jul. 18, 2019

(65) Prior Publication Data
US 2021/0196698 A1   Jul. 1, 2021

(30) Foreign Application Priority Data
Jan. 11, 2018   (IN) .............................. 201841001281

(51) Int. Cl.
*A61K 31/454* (2006.01)
*A61K 9/48* (2006.01)
*A61K 47/26* (2006.01)

(52) U.S. Cl.
CPC .......... *A61K 31/454* (2013.01); *A61K 9/4825* (2013.01); *A61K 9/4858* (2013.01); *A61K 47/26* (2013.01)

(58) Field of Classification Search
CPC .................................................. A61K 31/454
USPC ........................................................ 514/326
See application file for complete search history.

(56) References Cited

U.S. PATENT DOCUMENTS

| | | | | |
|---|---|---|---|---|
| 4,280,997 A | * | 7/1981 | Van Leverink | B29C 48/832 424/676 |
| 7,393,862 B2 | * | 7/2008 | Zeldis | A61P 35/02 514/315 |
| 8,877,932 B2 | * | 11/2014 | Konakanchi | C07D 401/04 546/201 |
| 8,946,265 B2 | | 2/2015 | Gore et al. | |
| 9,108,945 B2 | * | 8/2015 | Konakanchi | A61P 35/00 |
| 10,040,778 B2 | * | 8/2018 | Konakanchi | A61P 35/00 |
| 2017/0368197 A1 | | 2/2017 | Keltjens et al. | |

FOREIGN PATENT DOCUMENTS

| | | |
|---|---|---|
| CN | 103705485 B | 7/2015 |
| EP | 2875817 A1 | 5/2015 |
| WO | 98/03502 A1 | 1/1998 |
| WO | 2005023192 A3 | 3/2005 |
| WO | 2009114601 A2 | 9/2009 |
| WO | 2010054833 A1 | 5/2010 |
| WO | 2016097025 A1 | 6/2016 |
| WO | 2016097030 A1 | 6/2016 |
| WO | 2017032870 A1 | 3/2017 |
| WO | 2017109041 A1 | 6/2017 |

OTHER PUBLICATIONS

International Search Report and Written Opinion dated Apr. 9, 2019 from International Application No. PCT/IN2019/050012 (Authorized Officer, Kamalesh Kumar Patel), 8 pages.

* cited by examiner

*Primary Examiner* — Nizal S Chandrakumar
(74) *Attorney, Agent, or Firm* — MH2 Technology Law Group, LLP

(57) ABSTRACT

The present invention relates to pharmaceutical compositions comprising Lenalidomide. More particularly, the present invention relates to a stable composition comprising anhydrous Lenalidomide Form I and one or more pharmaceutically acceptable excipients and process for preparing such compositions.

3 Claims, No Drawings

STABLE PHARMACEUTICAL COMPOSITIONS COMPRISING LENALIDOMIDE

CROSS-REFERENCE TO RELATED APPLICATIONS

This application is a U.S. National Stage application of PCT/IN2019/050012 filed 7 Jan. 2019, which claims priority to Indian Application No. 201841001281 filed 11 Jan. 2018, the entire disclosures of which are hereby incorporated by reference in their entireties.

FIELD OF THE INVENTION

The present invention relates to pharmaceutical compositions comprising Lenalidomide. More particularly, the present invention relates to a stable composition comprising anhydrous Lenalidomide Form I and one or more pharmaceutically acceptable excipients and process for preparing such compositions.

BACKGROUND OF THE INVENTION

Lenalidomide, a thalidomide analogue, is an immunomodulatory agent with antiangiogenic and antineoplastic properties. It is chemically 3-(4-amino-1-oxo 1,3-dihydro-2H-isoindol-2-yl) piperidine-2,6-dione and is used for the treatment of Multiple Myeloma, Myelodysplastic Syndromes and Mantle Cell Lymphoma. It is marketed in the form of capsules under the brand name REVLIMID® by Celgene. Lenalidomide was first disclosed in WO 98/03502.

Lenalidomide exists in various solid forms. Various anhydrates and solvates are disclosed in WO 2005/023192. WO 2005/023192 discloses crystalline forms of Lenalidomide, its process of preparation, compositions comprising these crystalline forms and its use for treatment of diseases. Polymorph B is the most stable form and is present in the marketed dosage form. It further discloses that these forms can interconvert, e.g. hemihydrate B converts into dihydrate E in the presence of water, anhydrate A converts into form E in the presence of an amount of form E or in the presence of water.

WO 2010/054833 discloses a solid solution of Lenalidomide in a matrix material. These solid solutions are prepared using melt extrusion and spray drying. These pharmaceutical techniques have disadvantages: melt extrusion requires high temperatures. Since Lenalidomide has a high melting point, this may result in growing of impurities as a result of thermal decomposition. Also, the extrudates require milling in order to be useful for preparing pharmaceutical formulations thereof. Spray drying is disadvantageous, because in solvents that are suitable for spray drying, Lenalidomide has low solubility. Therefore, spray drying requires copious amounts of solvents, making the process unsuitable for carrying out on a commercial scale.

WO 2009/114601 discloses dispersions of amorphous Lenalidomide in povidone. During the process to prepare these dispersions, a mixture of dimethylformamide and methanol is used. Spray drying/evaporation at high temperatures is necessary to completely remove these solvents. Using methanol and dimethylformamide is undesirable, as these solvents are toxic and are undesirable for making a pharmaceutical product.

WO 2016/097025 A1 discloses a composition comprising an inclusion complex of amorphous lenalidomide, with a non-substituted β-cyclodextrin and one or more pharmaceutically acceptable excipients.

WO 2016/097030 A1 discloses a composition comprising an adsorbate of Lenalidomide on a porous carrier and one or more pharmaceutically acceptable excipients.

WO 2017/032870 A1 discloses pharmaceutical compositions comprising the active substance Lenalidomide in one of the modifications selected from Lenalidomide base, a Lenalidomide salt, a Lenalidomide cocrystal or mixtures thereof, wherein the Lenalidomide particles have a particle size distribution (d90) ranging from 1 μm to 100 μm.

WO 2017/109041 A1 discloses a pharmaceutical composition comprising amorphous Lenalidomide, or a pharmaceutically acceptable salt thereof, with a synthetic antioxidant and one or more pharmaceutically acceptable excipients.

US 2017/0368197 discloses a pharmaceutical composition comprising an inclusion complex of amorphous Lenalidomide, or a pharmaceutically acceptable salt thereof, in non-substituted β-cyclodextrin and one or more pharmaceutically acceptable excipients.

EP 2875817 A1 discloses a pharmaceutical composition comprising a solid composite consisting essentially of Lenalidomide ion exchange polymer complex and further discloses that the Lenalidomide present in the composition is in an amorphous form.

CN 103705485 discloses the use of beta cyclodextrins as solubilizing agent in Lenalidomide formulations in a ratio of 1:8.

U.S. Pat. No. 9,108,945 discloses anhydrous Lenalidomide Form I and process for its preparation. This patent also discloses a composition comprising anhydrous Lenalidomide Form I. The patent discloses that the sample of Lenalidomide Form I API is encapsulated & compared with the REVLIMID® capsules. However, there is no disclosure of any excipients used for the preparation of the composition. Further, there is no disclosure of any information relating to the stability of the compositions.

The above prior art references discloses different polymorphs of Lenalidomide and compositions comprising Lenalidomide. Still, there exists a need to develop an alternative stable dosage form comprising Lenalidomide. The inventors of the present invention have surprisingly found that a capsule composition comprising anhydrous Lenalidomide Form I and lactose anhydrous showed improved stability of Lenalidomide and does not show any change in polymorphic form after accelerated stability studies. Further, the inventors also found that due to the presence of less excipients, the total fill weight as well as capsule size is reduced, which will be convenient for intake by the patients and leads to increase in patient compliance.

OBJECTIVE OF THE INVENTION

The main objective of the present invention relates to a stable composition comprising anhydrous Lenalidomide Form I, at least one diluent and optionally one or more pharmaceutically acceptable excipients.

The present invention also relates to a stable capsule composition comprising anhydrous Lenalidomide Form I and lactose anhydrous.

The present invention also relates to a process for the preparation of a stable composition comprising anhydrous Lenalidomide Form I, at least one diluent and optionally one or more pharmaceutically acceptable excipients.

The present invention also relates to a process for the preparation of a stable capsule composition comprising anhydrous Lenalidomide Form I and lactose anhydrous having comparable dissolution properties, content uniformity and equivalent bioavailability w.r.t commercialized Lenalidomide dosage form.

SUMMARY OF THE INVENTION

Accordingly, the present invention provides a stable pharmaceutical composition comprising anhydrous Lenalidomide Form I, at least one diluent and optionally one or more pharmaceutically acceptable excipients.

The present invention also relates to a stable capsule composition comprising anhydrous Lenalidomide Form I and lactose anhydrous.

DETAILED DESCRIPTION OF THE INVENTION

The present invention relates to a stable pharmaceutical composition comprising Lenalidomide and one or more pharmaceutically acceptable excipients.

The present invention further relates to a stable pharmaceutical composition comprising anhydrous Lenalidomide Form I and one or more pharmaceutically acceptable excipients.

The present invention further relates to a stable pharmaceutical composition comprising anhydrous Lenalidomide Form I, at least one diluent and optionally one or more pharmaceutically acceptable excipients.

The present invention also relates a process for the preparation of a stable pharmaceutical composition comprising anhydrous Lenalidomide Form I, at least one diluent and optionally one or more pharmaceutically acceptable excipients.

In an embodiment, "Lenalidomide" according to the present invention includes but not limited to Lenalidomide and its pharmaceutically acceptable salts, ethers, esters, prodrugs and derivatives thereof.

"Pharmaceutically acceptable excipient/s" are the components added to pharmaceutical formulation to facilitate manufacture, enhance stability, control release, enhance product characteristics, enhance bioavailability, enhance patient acceptability, etc.

In another embodiment, the composition according to the present invention further comprises one or more pharmaceutically acceptable excipients which include but not limited to diluents, disintegrants, binders, surfactants, glidants and lubricants. These excipients may be present intragranularly or extragranularly.

Diluents according to the present invention include but not limited to lactose monohydrate, lactose anhydrous, fructose, dextrose, dextrates, dextrins, mannitol, lactitol, sorbitol, starch, sucrose, calcium carbonate, dibasic calcium phosphate, tribasic calcium phosphate, calcium sulfate, microcrystalline cellulose, silicified microcrystalline cellulose, cellulose powdered, kaolin and the like or combinations thereof.

Binders according to the present invention include but not limited to hydroxypropyl methylcellulose, hydroxypropyl cellulose, polyvinylpyrrolidone, gelatin, ethyl cellulose, polyvinyl alcohol, pregelatinized starch, carboxymethyl cellulose, sodium alginate, microcrystalline cellulose and the like or combinations thereof.

Disintegrants according to the present invention include but not limited to starches or modified starches such as pregelatinized starch, croscarmellose sodium, crospovidone, sodium starch glycolate, low substituted hydroxypropyl cellulose, hydroxypropyl cellulose and the like or combinations thereof.

Surfactants according to the present invention may be selected from anionic, cationic or non-ionic surface-active agents or surfactants. Suitable anionic surfactants include but not limited to carboxylate, sulfonate, and sulfate ions such as sodium lauryl sulfate (SLS), sodium laurate, dialkyl sodium sulfosuccinates particularly bis-(2-ethylhexyl) sodium sulfosuccinate, sodium stearate, potassium stearate, sodium oleate and the like. Suitable cationic surfactants include but not limited to those containing long chain cations, such as benzalkonium chloride, bis-2-hydroxyethyl oleyl amine or the like. Suitable non-ionic surfactants include but not limited to polyoxyethylene sorbitan fatty acid esters (polysorbates), fatty alcohols such as lauryl, cetyl and stearyl alcohols; glyceryl esters such as the naturally occurring mono-, di-, and tri-glycerides; fatty acid esters of fatty alcohols; polyglycolized glycerides such as gelucire; polyoxyethylene-polyoxypropylene block co-polymer such as Poloxamer and other alcohols such as propylene glycol, polyethylene glycol.

Lubricants/glidants according to the present invention include but not limited to colloidal silicon dioxide, stearic acid, magnesium stearate, calcium stearate, sodium stearyl fumarate, talc, hydrogenated castor oil, and mixtures thereof.

In one embodiment of the present invention, the stable composition comprises Lenalidomide in an amount of 0.1-20% w/w of the composition.

In another embodiment of the present invention, the stable composition comprises at least one diluent in an amount of 50-99.9 w/w of the composition.

In another embodiment, the present invention relates to a stable pharmaceutical composition comprising 1-20% w/w of anhydrous Lenalidomide Form I, 50-99% w/w of at least one diluent and optionally one or more pharmaceutically acceptable excipients.

In another embodiment, the present invention relates to a process for the preparation of stable pharmaceutical composition, comprising the steps of:
(i) blending anhydrous Lenalidomide Form I with at least one diluent and optionally one or more pharmaceutically acceptable excipients,
(ii) formulating the blend of step (i) into suitable dosage form.

In another embodiment, the present invention relates to a process for the preparation of stable pharmaceutical composition, comprising the steps of:
(i) blending anhydrous Lenalidomide Form I with at least one diluent,
(ii) optionally, lubricating the blended material of step (i) with a lubricant, and
(iii) preparing the lubricated material of step (ii) into suitable dosage form.

In another embodiment, the present invention relates to a process for the preparation of stable pharmaceutical composition, comprising the steps of:
(i) blending anhydrous Lenalidomide Form I with at least one diluent and optionally one or more pharmaceutically acceptable excipients,
(ii) compressing the blend of step (i) into tablet dosage form.

In another embodiment, the present invention relates to a process for the preparation of stable pharmaceutical composition, comprising the steps of:

(i) blending anhydrous Lenalidomide Form I with at least one diluent and optionally one or more pharmaceutically acceptable excipients,
(ii) granulating the blend of step (i),
(iii) blending the granules of step (ii) with one or more pharmaceutically acceptable excipients, and
(iv) compressing the lubricated blend of step (iii) into tablet dosage form.

In another embodiment, the present invention relates to a process for the preparation of stable pharmaceutical composition, comprising the steps of:
(i) blending anhydrous Lenalidomide Form I with at least one diluent, and
(iii) filling the blend of step (i) into capsules.

In another embodiment, the present invention relates to a process for the preparation of stable pharmaceutical composition, comprising the steps of:
(i) blending anhydrous Lenalidomide Form I with at least one diluent,
(ii) lubricating the blended material of step (iii) with a lubricant, and
(iii) filling the lubricated material of step (ii) into capsules.

In another embodiment, the pharmaceutical composition according to the present invention is in the form of tablets, capsules, granules, powder, pellets and sachets.

In another embodiment, the blend is formulated into a suitable dosage form like tablets or capsules using different techniques which are well known in the prior art.

In another embodiment, the compositions of the present invention may be prepared using any method known in the art, but are not limited to encapsulation, wet granulation, dry granulation and direct compression.

In another embodiment, the solvents used for granulation process may be selected from water, isopropyl alcohol, methanol, ethanol, methylene chloride or combination thereof.

The pharmaceutical composition may be further film coated with functional or non functional layer. The coating may be selected from amongst one or more of those suitable coating materials known in the art. For example, the coating material can be Opadry or Opadry AMB. Coating may be performed by applying one or more film forming polymers, with or without other pharmaceutically inert excipients, as a solution/suspension using any conventional coating technique known in the art, such as spray coating in a conventional coating pan or fluidized bed processor; or dip coating. Coloring agent may be selected from FDA approved colorants such as Iron Oxide, Lake of Tartrazine, Allura Red, Lake of Quinoline Yellow, Lake of Erythrosine, Titanium Dioxide and the like.

In one preferred embodiment, the pharmaceutical composition according to the present invention is in the form of capsules including but not limited to soft gelatin, hard gelatin, HPMC, polysaccharide or starch capsules as plugged, welded or glued capsules, of different size, colour, and water content. Preferably, the capsule are hard gelatin capsules.

In another preferred embodiment, the pharmaceutical composition according to the present invention is in the form of capsules.

In another preferred embodiment, the capsules are selected from hard gelatin capsules of Size 2 and Size 4.

In another preferred embodiment of the present invention, the at least one diluent is lactose anhydrous.

In another preferred embodiment, the present invention relates to a stable capsule composition comprising anhydrous Lenalidomide Form I and lactose anhydrous.

In another preferred embodiment, the present invention relates to a stable capsule composition consisting of anhydrous Lenalidomide Form I and lactose anhydrous.

In another preferred embodiment, the present invention relates to a stable capsule composition comprising 0.1-20% w/w of anhydrous Lenalidomide Form I and 80-99.9% w/w of lactose anhydrous.

In another preferred embodiment, the present invention relates to a stable capsule composition comprising 1-20% w/w of anhydrous Lenalidomide Form I and 80-99% w/w of lactose anhydrous.

In another preferred embodiment, the present invention relates to a stable capsule composition comprising anhydrous Lenalidomide Form I and lactose anhydrous, wherein the total fill weight of the capsule is less than 500 mg, preferable less than 400 mg and more preferably less than 300 mg.

In another preferred embodiment, the ratio of anhydrous Lenalidomide Form I and lactose anhydrous present in the capsule composition in the range of 1:5 to 1:30.

In another preferred embodiment, the present invention relates to a process for the preparation of stable capsule composition, comprising the steps of:
(i) blending anhydrous Lenalidomide Form I with lactose anhydrous,
(ii) filling the blend of step (i) into hard gelatin capsules.

As used herein, the term "stable" means less" than 1% of known and/or unknown impurities and less than 5% of total impurities.

In another embodiment, the present invention provides a stable capsule composition comprising anhydrous Lenalidomide Form I and lactose anhydrous, and the capsule composition is chemically stable when stored at 40° C./75% RH for 6 months.

In another embodiment, the present invention provides a stable capsule composition comprising anhydrous Lenalidomide Form I and lactose anhydrous, wherein the composition is filled into a hard gelatin capsules selected from Size 2 and Size 4 capsule.

In another embodiment, the present invention provides a stable capsule composition comprising anhydrous Lenalidomide Form I and lactose anhydrous, having a moisture content in the range of 0-10% w/w, preferably in the range of 0-5% w/w and more preferably in the range of 0-3% w/w.

In another embodiment, the present invention provides a stable capsule composition comprising anhydrous Lenalidomide Form I and lactose anhydrous, having assay in the range of 95.0% to 105.0%.

In another embodiment, the present invention provides a stable capsule composition comprising anhydrous Lenalidomide Form I and lactose anhydrous, having a dissolution not less than 80% of the labeled amount of Lenalidomide in 30 minutes.

In another embodiment, the present invention provides a stable capsule composition comprising anhydrous Lenalidomide Form I and lactose anhydrous, and the said capsule comprising not more than about 0.5% of known impurities, not more than about 0.20% of any individual unknown impurity and not more than about 1.50% of total impurity.

In yet another embodiment, the present invention provides a stable capsule composition comprising anhydrous Lenalidomide Form I in the range of about 0.01 mg to about 100 mg.

In another embodiment, the present invention provides a stable capsule composition comprising anhydrous Lenalidomide Form I and lactose anhydrous for the treatment of Multiple Myeloma, Myelodysplastic Syndromes and Mantle Cell Lymphoma.

The invention is further illustrated by the following examples which are provided to be exemplary of the invention and do not limit the scope of the invention. While the present invention has been described in terms of its specific embodiments, certain modifications and equivalents will be apparent to those skilled in the art and are intended to be included within the scope of the present invention.

Examples 1-7: Capsule Compositions Comprising Anhydrous Lenalidomide Form I

| S. No | Ingredients | Ex-1 | Ex-2 | Ex-3 | Ex-4 | Ex-5 | Ex-6 | Ex-7 |
|---|---|---|---|---|---|---|---|---|
| | | Quantity (mg/capsule) | | | | | | |
| 1 | Anhydrous Lenalidomide Form I | 2.50 | 5.00 | 7.50 | 10.00 | 15.00 | 20.00 | 25.00 |
| 2 | Lactose anhydrous | 43.33 | 86.66 | 130.00 | 173.33 | 260.00 | 255.00 | 250.00 |
| | Total fill weight | 45.83 | 91.66 | 137.5 | 183.33 | 275.00 | 275.00 | 275.00 |
| | Hard Gelatin Capsule | Size "4" | Size "2" | Size "2" | Size "2" | Size "2" | Size "2" | Size "2" |

The processing steps involved in manufacturing Lenalidomide capsules of Examples 1-7 were given below:

(i) Lenalidomide and lactose anhydrous were blended, (ii) the blend of step (i) was filled into hard gelatin capsule.

Dissolution Data: Tables 1-7 given below provides the comparative dissolution profile of Lenalidomide Capsules prepared according to examples 1-7 and REVLIMID® capsules carried out in 900 ml of 0.01N HCl as dissolution medium in USP II apparatus (paddle) at 50 rpm.

TABLE 1

Comparative dissolution profile of Lenalidomide 2.5 mg capsules prepared according to Example 1 and REVLIMID ® 2.5 mg capsules

| | Cumulative % drug released | |
|---|---|---|
| Time (Minutes) | REVLIMID ® 2.5 mg capsules | Lenalidomide 2.5 mg capsules prepared according to Example 1 |
| 5 | 71.7 | 69.6 |
| 10 | 97.7 | 96.2 |
| 15 | 98 | 98.7 |
| 20 | 97 | 99.2 |
| 30 | 97.4 | 99.4 |
| 45 | 96.8 | 99.3 |

TABLE 2

Comparative dissolution profile of Lenalidomide 5 mg capsules prepared according to Example 2 and REVLIMID ® 5 mg capsules

| | Cumulative % drug released | |
|---|---|---|
| Time (Minutes) | REVLIMID ® 5 mg capsules | Lenalidomide 5 mg capsules prepared according to Example 2 |
| 5 | 81.6 | 80.9 |
| 10 | 96.2 | 89.3 |
| 15 | 97.2 | 94.7 |
| 20 | 97.9 | 97.4 |
| 30 | 98 | 99.1 |
| 45 | 98.1 | 99.5 |

TABLE 3

Comparative dissolution profile of Lenalidomide 7.5 mg capsules prepared according to Example 3 and REVLIMID ® 7.5 mg capsules

| | Cumulative % drug released | |
|---|---|---|
| Time (Minutes) | REVLIMID ® 7.5 mg capsules | Lenalidomide 7.5 mg capsules prepared according to Example 3 |
| 5 | 76.7 | 74.5 |
| 10 | 98.2 | 92.4 |
| 15 | 99.6 | 95.9 |
| 20 | 99.8 | 98.2 |
| 30 | 99.9 | 101.3 |
| 45 | 100.4 | 101.1 |

TABLE 4

Comparative dissolution profile of Lenalidomide 10 mg capsules prepared according to Example 4 and REVLIMID ® 10 mg capsules

| | Cumulative % drug released | |
|---|---|---|
| Time (Minutes) | REVLIMID ® 10 mg capsules | Lenalidomide 10 mg capsules prepared according to Example 4 |
| 5 | 69.6 | 71.3 |
| 10 | 88.8 | 93.1 |
| 15 | 91.4 | 95.3 |
| 20 | 93.5 | 96.9 |
| 30 | 95 | 99 |
| 45 | 95.8 | 99.5 |

TABLE 5

Comparative dissolution profile of Lenalidomide 15 mg capsules prepared according to Example 5 and REVLIMID ® 15 mg capsules

| | Cumulative % drug released | |
|---|---|---|
| Time (Minutes) | REVLIMID ® 15 mg capsules | Lenalidomide 15 mg capsules prepared according to Example 5 |
| 5 | 69.9 | 75.7 |
| 10 | 93.1 | 92.3 |
| 15 | 98.8 | 95.9 |

TABLE 5-continued

Comparative dissolution profile of Lenalidomide 15 mg capsules prepared according to Example 5 and REVLIMID® 15 mg capsules

| Time (Minutes) | Cumulative % drug released | |
|---|---|---|
| | REVLIMID® 15 mg capsules | Lenalidomide 15 mg capsules prepared according to Example 5 |
| 20 | 99.1 | 98.3 |
| 30 | 99 | 100.2 |
| 45 | 99.1 | 100.1 |

TABLE 6

Comparative dissolution profile of Lenalidomide 20 mg capsules prepared according to Example 6 and REVLIMID® 20 mg capsules

| Time (Minutes) | Cumulative % drug released | |
|---|---|---|
| | REVLIMID® 20 mg capsules | Lenalidomide 20 mg capsules prepared according to Example 6 |
| 5 | 79.6 | 76.9 |
| 10 | 94.3 | 93.3 |
| 15 | 94.2 | 98.2 |
| 20 | 94.9 | 100 |
| 30 | 95.8 | 101 |
| 45 | 96.7 | 101.5 |

TABLE 7

Comparative dissolution profile of Lenalidomide 25 mg capsules prepared according to Example 7 and REVLIMID® 25 mg capsules

| Time (Minutes) | Cumulative % drug released | |
|---|---|---|
| | REVLIMID® 25 mg capsules | Lenalidomide 25 mg capsules prepared according to Example 7 |
| 5 | 92.5 | 88.3 |
| 10 | 99.3 | 98.2 |
| 15 | 100.2 | 102.3 |
| 20 | 100.1 | 103.2 |
| 30 | 100 | 102.6 |
| 45 | 99.9 | 102.3 |

Stability Data: Tables 8-14 given below shows the impurity profile of Lenalidomide capsules prepared according to the present invention (Examples 1-7) after storing at 40° C./75% RH for 6 months.

TABLE 8

Stability data of Lenalidomide 2.5 mg capsules prepared according to Example 1 after storing at 40° C./75% RH for 6 months

| Impurities | Limits (% w/w) | Initial | 3 months | 6 months |
|---|---|---|---|---|
| Assay | 95.0% to 105.0% | 101.3% | 100.8% | 100.7% |
| Water content | NMT 3.0% w/w | 0.04% | 0.03% | 0.04% |
| Impurity A | Not more than 0.5% | ND | ND | ND |
| Impurity B | Not more than 0.5% | <LOQ (0.016%) | <LOQ (0.016%) | <LOQ (0.016%) |
| Impurity C1 (E) | Not more than 0.5% | 0.07% | 0.12% | 0.10% |
| Impurity C2 (Z) | Not more than 0.5% | 0.05% | 0.14% | 0.12% |
| Unknown Impurity | Not more than 0.2% | <0.05% | <0.05% | <0.05% |
| Total Impurities | Not more than 1.5% | 0.11% | 0.25% | 0.22% |

TABLE 9

Stability data of Lenalidomide 5 mg capsules prepared according to Example 2 after storing at 40° C./75% RH for 6 months

| Impurities | Limits (% w/w) | Initial | 3 months | 6 months |
|---|---|---|---|---|
| Assay | 95.0% to 105.0% | 99.8% | 100.6% | 100.9% |
| Water content | NMT 3.0% w/w | 0.04% | 0.03% | 0.03% |
| Impurity A | Not more than 0.5% | ND | ND | ND |
| Impurity B | Not more than 0.5% | <LOQ (0.016%) | <LOQ (0.016%) | <LOQ (0.016%) |
| Impurity C1 (E) | Not more than 0.5% | 0.11% | 0.14% | 0.12% |
| Impurity C2 (Z) | Not more than 0.5% | 0.09% | 0.16% | 0.15% |
| Unknown Impurity Maximum | Not more than 0.2% | <0.05% | <0.05% | <0.05% |
| Total Impurities | Not more than 1.5% | 0.20% | 0.29% | 0.27% |

TABLE 10

Stability data of Lenalidomide 7.5 mg capsules prepared according to Example 3 after storing at 40° C./75% RH for 6 months

| Impurities | Limits (% w/w) | Initial | 3 months | 6 months |
|---|---|---|---|---|
| Assay | 95.0% to 105.0% | 99.4% | 98.6% | 100.5% |
| Water content | NMT 3.0% w/w | 0.03% | 0.02% | 0.06% |
| Impurity A | Not more than 0.5% | ND | ND | ND |
| Impurity B | Not more than 0.5% | <LOQ (0.016%) | <LOQ (0.016%) | <LOQ (0.016%) |
| Impurity C1 (E) | Not more than 0.5% | <LOQ (0.030%) | 0.09% | 0.09% |
| Impurity C2 (Z) | Not more than 0.5% | <LOQ (0.030%) | 0.11% | 0.10% |
| Unknown Impurity Maximum | Not more than 0.2% | <0.05% | <0.05% | <0.05% |
| Total Impurities | Not more than 1.5% | <0.05% | 0.20% | 0.19% |

TABLE 11

Stability data of Lenalidomide 10 mg capsules prepared according to Example 4 after storing at 40° C./75% RH for 6 months

| Impurities | Limits (% w/w) | Initial | 3 months | 6 months |
|---|---|---|---|---|
| Assay | 95.0% to 105.0% | 100.4% | 99.1% | 101.2% |
| Water content | NMT 3.0% w/w | 0.03% | 0.02% | 0.05% |

TABLE 11-continued

Stability data of Lenalidomide 10 mg capsules prepared according to Example 4 after storing at 40° C./75% RH for 6 months

| Impurities | Limits (% w/w) | Initial | 3 months | 6 months |
|---|---|---|---|---|
| Impurity A | Not more than 0.5% | ND | ND | ND |
| Impurity B | Not more than 0.5% | <LOQ (0.016%) | <LOQ (0.016%) | <LOQ (0.016%) |
| Impurity C1 (E) | Not more than 0.5% | 0.06% | 0.09% | 0.07% |
| Impurity C2 (Z) | Not more than 0.5% | 0.05% | 0.12% | 0.09% |
| Unknown Impurity Maximum | Not more than 0.2% | <0.05% | <0.05% | <0.05% |
| Total Impurities | Not more than 1.5% | 0.11% | 0.20% | 0.16% |

TABLE 12

Stability data of Lenalidomide 15 mg capsules prepared according to Example 5 after storing at 40° C./75% RH for 6 months

| Impurities | Limits (% w/w) | Initial | 3 months | 6 months |
|---|---|---|---|---|
| Assay | 95.0% to 105.0% | 98.4% | 101.0% | 99.8% |
| Water content | NMT 3.0% w/w | 0.17% | 0.10% | 0.05% |
| Impurity A | Not more than 0.5% | ND | ND | ND |
| Impurity B | Not more than 0.5% | ND | ND | ND |
| Impurity C1 (E) | Not more than 0.5% | 0.04% | 0.13% | 0.18% |
| Impurity C2 (Z) | Not more than 0.5% | | | |
| Unknown Impurity Maximum | Not more than 0.2% | <0.05% | <0.05% | <0.05% |
| Total Impurities | Not more than 1.5% | 0.04% | 0.13% | 0.18% |

TABLE 13

Stability data of Lenalidomide 20 mg capsules prepared according to Example 6 after storing at 40° C./75% RH for 6 months

| Impurities | Limits (% w/w) | Initial | 3 months | 6 months |
|---|---|---|---|---|
| Assay | 95.0% to 105.0% | 98.8% | 100.3% | 99.7% |
| Water content | NMT 3.0% w/w | 0.06% | 0.12% | 0.12% |

TABLE 13-continued

Stability data of Lenalidomide 20 mg capsules prepared according to Example 6 after storing at 40° C./75% RH for 6 months

| Impurities | Limits (% w/w) | Initial | 3 months | 6 months |
|---|---|---|---|---|
| Impurity A | Not more than 0.5% | ND | ND | ND |
| Impurity B | Not more than 0.5% | ND | ND | ND |
| Impurity C1 (E) | Not more than 0.5% | <LOQ (0.030%) | <LOQ (0.030%) | <LOQ (0.030%) |
| Impurity C2 (Z) | Not more than 0.5% | <LOQ (0.030%) | 0.03% | <LOQ (0.030%) |
| Unknown Impurity Maximum | Not more than 0.2% | <0.05% | <0.05% | <0.05% |
| Total Impurities | Not more than 1.5% | <0.05% | 0.03% | <0.05% |

TABLE 14

Stability data of Lenalidomide 25 mg capsules prepared according to Example 7 after storing at 40° C./75% RH for 6 months

| Impurities | Limits (% w/w) | Initial | 3 months | 6 months |
|---|---|---|---|---|
| Assay | 95.0% to 105.0% | 101.6% | 101.2% | 98.0% |
| Water content | NMT 3.0% w/w | 0.19% | 0.04% | 0.08% |
| Impurity A | Not more than 0.5% | ND | ND | ND |
| Impurity B | Not more than 0.5% | ND | ND | ND |
| Impurity C1 (E) | Not more than 0.5% | 0.03% | 0.13% | 0.16% |
| Impurity C2 (Z) | Not more than 0.5% | | | |
| Unknown Impurity Maximum | Not more than 0.2% | <0.05% | <0.05% | <0.05% |
| Total Impurities | Not more than 1.5% | 0.03% | 0.13% | 0.16% |

The invention claimed is:

1. A capsule containing a stable composition consisting of anhydrous Lenalidomide Form I and lactose anhydrous.

2. A process for the preparation of the capsule as claimed in claim 1, comprising the steps of:
   (i) blending anhydrous Lenalidomide Form I with lactose anhydrous, and
   (ii) filling the blend of step (i) into hard gelatin capsules.

3. The capsule as claimed in claim 1, wherein the capsule are is selected from hard gelatin capsules of Size 2 and Size 4.

* * * * *